US007335735B2

(12) United States Patent
Adams et al.

(10) Patent No.: US 7,335,735 B2
(45) Date of Patent: Feb. 26, 2008

(54) INTRACELLULAR ESTRADIOL BINDING PROTEIN

(75) Inventors: John S. Adams, Los Angeles, CA (US); Hong Chen, Northridge, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 559 days.

(21) Appl. No.: 10/840,038

(22) Filed: May 6, 2004

(65) Prior Publication Data

US 2005/0009137 A1 Jan. 13, 2005

Related U.S. Application Data

(60) Provisional application No. 60/468,717, filed on May 7, 2003.

(51) Int. Cl.
C07K 14/705 (2006.01)
(52) U.S. Cl. .......................................... 530/350; 514/2
(58) Field of Classification Search .................... None
See application file for complete search history.

(56) References Cited

U.S. PATENT DOCUMENTS

| | | | |
|---|---|---|---|
| 5,639,741 A | 6/1997 | Witzel et al. |
| 5,962,667 A | 10/1999 | Jain et al. |
| 6,476,196 B1 | 11/2002 | Ljunggren et al. |
| 6,528,676 B1 | 3/2003 | D'Amato et al. |
| 6,531,149 B1 | 3/2003 | Kirstgen et al. |

OTHER PUBLICATIONS

Bowie et al. (1990) Science 247: 1306-1310.*
Brown, et al., Pituitary-Adrenal Function in the Squirrel Monkey, (1970) Endocrinology 86, 519-529.
Chrousos, et al., Glucocorticoid Hormone Resistance During Primate Evolution: Receptor-Mediated Mechanisms, (1982) Proc. Natl. Acad. Sci. U.S.A. 79, 2036-2040.
Chrousos, et al., Uterine Estrogen and Progesterone Receptors in an Estrogen- and Progesterone- "Resistant" Primate, (1984) J. Clinl Endocrinol. 58, 516-520.
Chrousos, et al., Adaptation of the Mineralocorticoid Target Tissues to the High Circulating Cortisol and Progesterone Plasma Levels in the Squirrel Monkey, (1984) Endocrinology 115,25-32.
Chrousos, et al., Uterine Estrogen and Progesterone Receptors in an Estrogen- and Progesterone- "Resistant" Primate, (1984) J. Clin. Endocrinol. Metab. 58, 516-520.
Chrousos, et al., The Squirrel Monkey: Receptor-Mediated End-Organ Resistance in Progesterone?, (1985) J. Clin. Endocrinol. Metab. 55, 364-368.
Takahashi, et al., The Mechanism of End-Organ Resistance to 1α,25-dihydroxycholecalciferol in the Common Marmoset, (1985) Biochem. J. 227, 555-563.
Adams, et al., Serum Concentrations of 1,25-dihydroxyvitamin $D_3$ in Playyrrhini and Catarrhini: A Phylogenetic Appraisal, (1985) Am. J. Primatol. 9, 219-224.
Siiteri, P. K., High Plasma Steroid Levels in the Squirrel Monkey: Deficient Receptors or Metabolisms?, (1986) Adv. Exp. Med. Biol. 196, 276-286.
Gacad, et al., Influence of Ultraviolet B Radiation on Vitamin $D_3$ Metabolism in Vitamin $D_3$-Resistant New World Primates, (1992) Am. J. Primatol. 28, 263-270.
Reynolds, et al., Glucocorticoid Resistance in the Squirrel Monkey is Associated with Overexpression of the Immunophilin FKBP51, (1999) J. Clin. Endocrinol. Metab. 84, 663-669.
Reynolds, et al., Cloning and Expression of the Glucocorticoid Receptor from the Squirrel Monkey (Saimiri boliviensis boliviensis), a Glucocorticoid-Resistant Primate, (1997) J. Clin. Endo. Metab. 82, 465-472.
Chun, et al., Cloning, Sequencing, and Functional Characterization of the Vitamin D Receptor in Vitamin D-Resistant New World Primates (2001) Am. J. Primatol. 54, 107-118.
Bonnegard, et al., The Genetic Basis of Glucocorticoid Resistance, (1995) Trends. Endocrinol. Metab. 6, 160-164.
Denny, et al., Squirrel Monkey Immunphilin FKBP51 Is a Potent Inhibitor of Glucocorticoid Receptor Binding, (2000) Endocrinol. 141, 4107-4113.
Chen, et al., The Vitamin D Response Element-Binding Protein, (2000) J. Biol. Chem. 275, 35557-35564.
Chen, et al., Vitamin D and Gonadal Steroid-Resistant New World Primate Cells Express an Intracellular Protein Which Competes with the Estrogen Receptor for Binding to the Estrogen Response Element, (1997) J. Clin. Invest. 99, 669-675.
Chen, et al., Cloning and Expression of a Novel Dominent-Negative-acting Estrogen Response Element-binding Protein in the Heterogeneous Nuclear Ribonucleoprotein Family, (1998) J. Biol. Chem. 273, 31352-31357.
Chen, et al., Purification and Characterization of a Novel Intracellular 17β-Estradiol Binding Protein in Estrogen-Resistant New World Primate Cells, (2003) J. Clin. Endocrinol. Metab. 88, 501-504.
Gacad, et al., Functional Characterization and Purification of an Intracellular Vitamin D-binding Protein in Vitamin D-resistant New World Primate Cells, (1997) J. Biol. Chem. 272, 8433-8440.
Wu, et al., Intracullular Vitamin D Binding Proteins: Novel Facilitators of Vitamin D-Directed Transactivation, (2001) Mol. Endocrinol. 14, 1387-1397.

(Continued)

Primary Examiner—Michael Pak
(74) Attorney, Agent, or Firm—Seth D. Levy; Davis Wright Tremaine LLP

(57) ABSTRACT

Described herein is a novel intracellular estradiol binding protein ("IEBP"), as well as a polynucleotide encoding this protein and various cells and cell lines producing and/or overexpressing it. IEBP is believed to play a role in the modulation of estrogen signaling and in the physiological resistance to the same. Abnormally elevated or decreased levels of IEBP may thus be a component of the etiology of diseases generally correlated with estrogen signaling, such as, by way of example, breast cancer and osteoporosis. Various embodiments of the present invention are believed to provide important tools for developing treatments for these conditions, such as, for example, by providing means for screening therapeutic compounds and identifying a genetic target for therapy.

7 Claims, 8 Drawing Sheets-

OTHER PUBLICATIONS

Gacad, et al., Proteins in the Heat Shock-70 Family Specifically Bind 25-Hydroxyvitamin $D_3$ and 17β-Estradiol, (1998) *J. Clin. Endocrinol. Metab.* 83,1264-1267.

Pasta, et al., Role of the Conserved SRLFDQFFG Region of a α-Crystallin, a Small Heat Shock Protein, (2003) *J Biol Chem* 278, 51159-51166.

Bullard, et al., Association of the Chaperone αB-crystallin with Titin in Heart Muscle, (2004), *J Biol Chem.* 279, 7917-7924.

Sathish, et al., Mechanism of Chaperone Function in Small Heat-shock Proteins, (2003) *J Biol Chem.* 278, 44214-21.

Bhattacharyya, et al., Cloning and Subcellular Localization of Human Mitochondrial hsp70, (1995) *J. Biol Chem* 270, 1705-1710.

Tamrazi, et al., Estrogen Receptor Dimerization: Ligand Binding Regulates Dimer Affinity and Dimer Dissociation Rate, (2002) *Mol Endocrinol.* 16, 2706-2719.

Greene, et al., Sequence and Expression of Human Estrogen Receptor Complementary DNA, (1986) *Science* 231 (4742), 1150-1154.

Hickey, et al., Sequence and Organization of Genes Encoding the Human 27 kDa Heat Shock Protein, (1986) *Nucleic Acid Res.* 14, 4127-4145.

Witek, A., Typy Alternatywnego Skladania Receptorów Estrogenowych Alfa I Beta, (2003) *Ginekol PolMar* 74, 246-51.

Ferro, et al., Alternative Splicing of the Human Estrogen Receptor α Primary Transcript: Mechanisms of Exon Skipping, (2003) *Int J Mol Med.* 12, 355-63.

Mckenna, et al., Nuclear Receptor Coregulators: Cellular and Molecular Biology, (1999) *Endocrine Reviews* 20, 321-344.

Kumar, et al., The Structure of the Nuclear Hormone Receptors, (1999) *Steroids* 64, 310-319.

Klein-Hitpass, et al., Targets of Activated Steroid Hormone Receptors: Basal Transcription Factors and Receptor Interacting Proteins, (1998) *J. Mol. Med.* 76, 490-496.

Simpson, et al., Minireview: Aromatase and the Regulation of Estrogen Biosynthesis—Some New Perspectives, (2001) *Endocrinol.* 142, 4589-4594.

Labrie, et al., Intracrinology: role of the family of 17β-hydroxysteroid dehydrogenases in human physiology and disease, (2000) *J. Mol. Endocrinol.* 25,1-16.

Kumar, et al., The Estrogen Receptor Binds Tightly to Its Responsive Element as a Ligand-Induced Homodimer, (1988) *Cell* 55,145-156.

Wood, et al., Estrogen Response Elements Function as Allosteric Modulators of Estrogen Receptor Conformation, (1998) *Mol Cell Biol* 18, 1927-1934.

Chen, et al., Heterogeneous Nuclear Ribonucleoprotein (hnRNP) binding to hormone response elements: A cause of vitamin D resistance, (2003) *Proc. Natl. Acad. Sci. USA* 100, 6109-6114.

Wu, et al., Regulation of 1,25-Dihydroxyvitamin D Synthesis by Intracellular Vitamin D Binding Protein-1, (2002). *Endocrinology* 143,4135-4138.

Adams, et al., Novel Regulators of Vitamin D Action and Metabolism: Lessons Learned at the Los Angeles Zoo, (2003) *J Cell Biochem.* 88, 308-314.

Ciocca, et al., Biological and Clinical Implications of Heat Shock Protein 27000 (Hsp27): a Review, (1993). *J Natl Cancer Inst* 85, 1558-1570.

De Jong, et al., Genealogy of the α-crystallin—small heat-shock protein superfamily, (1998). *Int J Biol Macromol* 22, 151-162.

Narberhaus, α-Crystallin-Type heat Shock Proteins: Socializing Minichaperones in the Context of a Multichaperone Network, (2002). *Microbiol Mol Biol Rev* 66, 64-93.

Schlesinger, et al., Heat Shock Proteins, (1990). *J Biol Chem* 265, 12111-12114.

Stock, et al., *Heat Shock Protein 27* Gene: Chromosomal and Molecular Location and Relationship to Williams Syndrome, (2003). *Am J Med Genet* 120, 320-325.

Welsh, et al., Small Heat-Shock Protein Family: Function in Health and Disease, (1998). *Ann N Y Acad Sci* 851, 28-35.

Young, et al., Molecular Chaperones Hsp90 and Hsp70 Deliver Preproteins to the Mitochondrial Import Receptor Tom70, (2003) *Cell.* 112, 41-50.

Concannon, et al., On the Role of Hsp27 in Regulating Apoptosis, (2003). *Apoptosis* 8, 61-70.

Gerthoffer, et al., *Signal Transduction in Smooth Muscle* Invited Review: Focal adhesion and small heat shock proteins in the regulation of actin remodeling and contractility in smooth muscle, (2001). *J Appl Physiol* 91, 963-72.

Jia, et al., Identification and Characterization of hic-5/ARA55 as an hsp27 Binding Protein, (201). *J Biol Chem* 276, 39911-8.

Haslbeck, M., sHsps And Their Role in the Chaperone Network, (2002). *Cell Mol Life Sci* 59, 1649-1657.

Fu, et al., Enhanced Stability of αB-Crystallin in the Presence of Small Heat Shock Protein Hsp27, (2003) *Biochem Biophys Res Commun* 302, 710-714.

MacRae, T. H., Structure and Function of Small Heat Shock/α-Crystallin Proteins: Established Concepts and Emerging Ideas, (2000) *Cell Mol Life Sci* 57, 899-913.

Oesterreich, et al., The Small Heat Shock Protein HSP27 Is Not an Independent Prognostic Marker in Axillary Lymph Node-negative Breast Cancer Patients, (1996). *Clin Cancer Res* 2, 1199-1206.

Porter, et al., Role of Estrogen Receptor/Sp1 Complexes in Estrogen-Induced Heat Shock Protein 27 Gene Expression, (1996) *Mol Endocrinol.* 10, 1371-8.

Porter, et al., Transcriptional activation of heat shock protein 27 gene expression by 17β-estradiol and modulation by antiestrogens and aryl hydrocarbon receptor agonists, (2001). *J Mol Endocrinol.* 26, 31-42.

Hutchison, et al., Regulation of Glucocorticoid Receptor Function through Assembly of a Receptor-Heat Shock Protein Complex, (1993) *Ann. N. Y. Acad. Sci.* 684, 35-48.

Sabbah, et al., The 90 kDa heat-shock protein (hsp90) modulates the binding of the oestrogen receptor to its cognate DNA, (1996) *Biochem. J.* 314, 205-213.

Clemmons, et al., Insulin-Like Growth Factor Binding Protein Secretion by Breast Carcinoma Cell Lines: Correlation with Estrogen Receptor Status, 1990 *Endocrinology.* 127, 2679-2686.

Smith, et al., Chemoprevention of Breast Cancer by Tamoxifen: Risks and Opportunities, (2000) *Crit Rev Toxicol.* 30, 571-594.

Riggs, et al., Selective Estrogen-Receptor Modulators—Mechanisms of Action of Application to Clinical Practice, (2003) *N Engl J Med.* 348, 618-629.

Takahashi, et al., Immunohistochemical Detection of Estrogen Receptor in Invasive Human Breast Cancer: Correlation with Heat Shock Proteins, pS2 and Oncogene Products, (1995) *Oncol.* 52, 371-375.

Munoz de Toro, et al., Lack of Relationship Between the Expression of Hsp27 Heat Shock Estrogen Receptor-associated Protein and Estrogen Receptor or Progesterone Receptor Status in Male Breast Carcinoma (1997) *J. Steroid Biochem. Mol. Biol.* 60, 277-284.

Frye, et al., Enhancing effects of estrogen on inhibitory avoidance performance may be in part independent of intracellular estrogen receptors in the hippocampus, 2002 *Brain Res* 956, 285-293.

Ciana, et al., In vivo imaging of transcriptionally active estrogen receptors, 2003, *Nat Med*, 9, 82-86.

Chen, et al., Purification and characterization of a novel intracellular 17 beta-estradiol binding protein in estrogen-resistant New World primate calls, 2003, *J Clin Endocrinol Metab.*, 88, 501-504.

Chen, H. et al., Functional characterization of the intracellular estradiol binding protein in estrogen resistant New World primates, Journal of Bone and Mineral Research, vol. 17, No. Suppl. 1, Sep. 2002, pp. S216-S217, XP009082776.

Chen, H. et al., A Hsp27-related, dominant-negative-acting intracellular estradiol-binding protein, Journal of Biological Chemistry, vol. 279, No. 29, Jul. 16, 2004, pp. 29944-29951, XP002430752.

* cited by examiner

Fig. 1A

```
IEBP     1    MTERHVPFSLLQSPSW..DPFRDWYPHSHLFDQAFGMPRLPEEWSQWFGT
hsp27         MTERRVPFSLLRGPSW..DPFRDWYPHSRLFDQAFGLPRLPEEWSQWLGG
hCrysA        ~~~~~~MDVTIQHPWFKRTLGPFY.PSRLFDQFFGEGLFEYDLLPFLSS
hCrysB        ~~~~~~MDIAIHHPWIRRPFFPFHSPSRLFDQFFGEHLLESDLFP.TST IEBP    51    SSWPGYVRPLPPTTVEGPAVAAPAYSRALNQQLSSGVSE...TADRWRVS
hsp27         SSWPGYVRPLPPAAIESPAVAAPAYSRALSRQLSSGVSEIRHTADRWRVS
hCrysA        TISPYYRQ..............SLFR..T.VLDSGISEVRSDRDKFVIF
hCrysB        SLSPFYLRP.............PSFLRAPS.WFDTGLSEMRLEKDRFSVN IEBP   101    LDVNHFAPEELTVKTKDGVVEITGKHEERQDEHGFISRCFTRKYSLPPGV
hsp27         LDVNHFAPDELTVKTKDGVVEITGKHEERQDEHGYISRCFTRKYTLPPGV
hCrysA        LDVKHFSPEDLTVKVQDDFVEIHGKHNERQDDHGYISREFHRRYRLPSNV
hCrysB        LDVKHFSPEELKVKVLGDVIEVHGKHEERQDEHGFISREFHRKYRIPADV IEBP   151    DPTQVSPSLSPEGTLTVDAPMSKPATQSN..EITIPVTFESR.AQLGGPE
hsp27         DPTQVSSSLSPEGTLTVEAPMPKLATQSN..EITIPVTFESR.AQLGGPE
hCrysA        DQSALSCSLSADGMLTFCGPKIQTGLDATHAERAIPVSREEKP..TSAPS
hCrysB        DPLTITSSLSSDGVLTVNGPRKQ....VSGPERTIPITREEKPAVTAAPK IEBP   201    AAKSDRSAAK
hsp27         AAKSDETAAK
hCrysA        S~~~~~~~~~
hCrysB        K~~~~~~~~~
```

Fig. 1B

|        | hsp27 | hCrys A | hCrys B |
|--------|-------|---------|---------|
| IEBP   | 87%   | 40%     | 44%     |
| hCrys A| 41%   |         | 54%     |
| hCrys B| 44%   | 54%     |         |

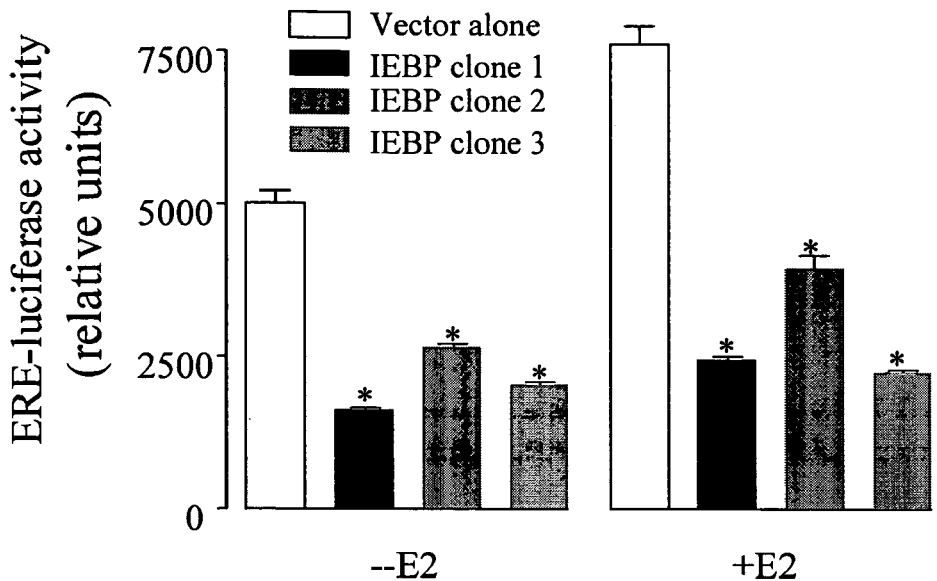
A.
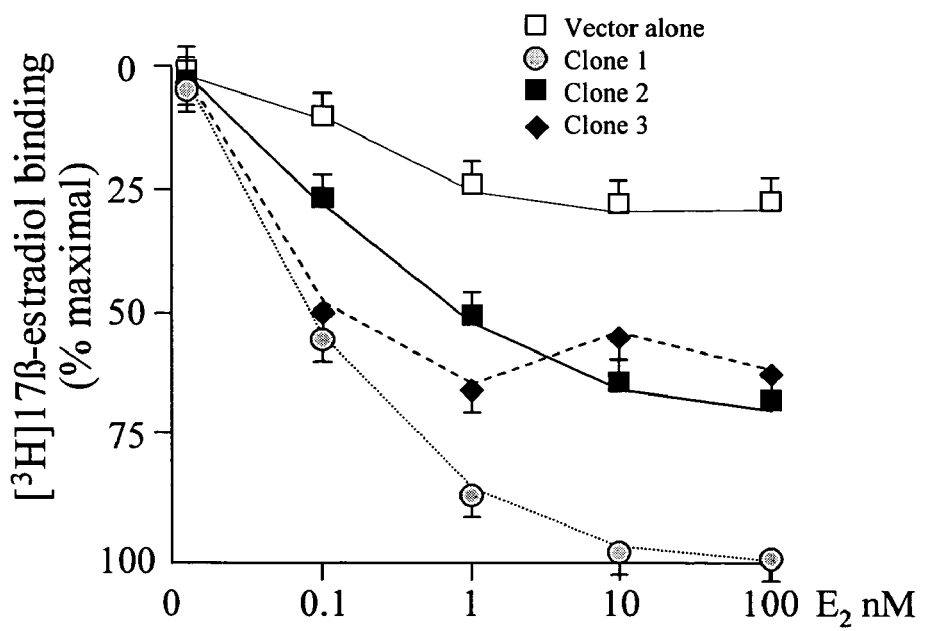
B.
Fig. 3

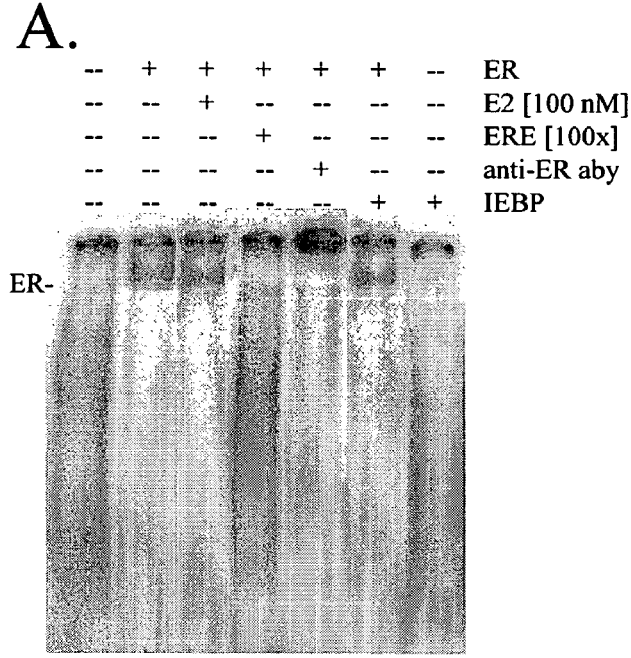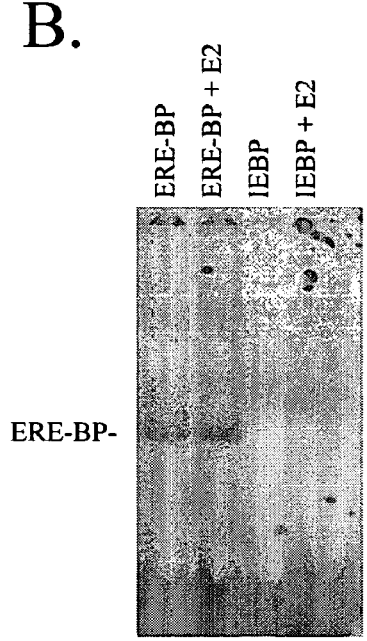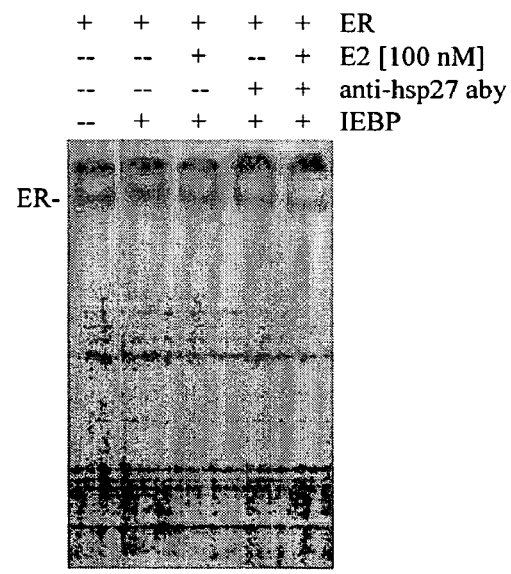
Fig. 4

A.
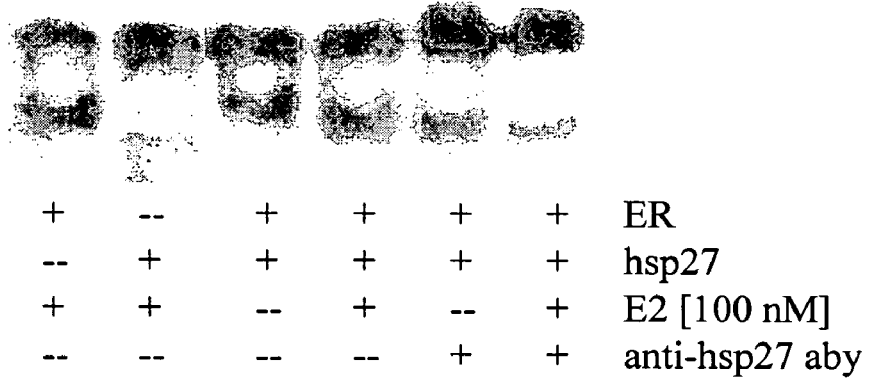
| | | | | | | |
|---|---|---|---|---|---|---|
| + | -- | + | + | + | + | ER |
| -- | + | + | + | + | + | hsp27 |
| + | + | -- | + | -- | + | E2 [100 nM] |
| -- | -- | -- | -- | + | + | anti-hsp27 aby |
B.
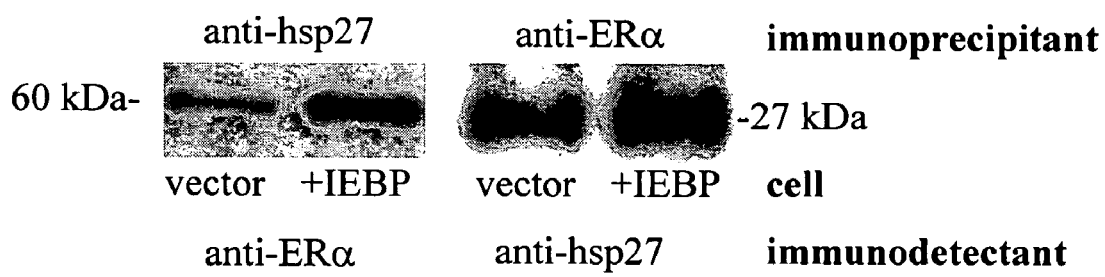
Fig. 5

A.
E2 [0.1-100 nM]
-27 kDa
B.
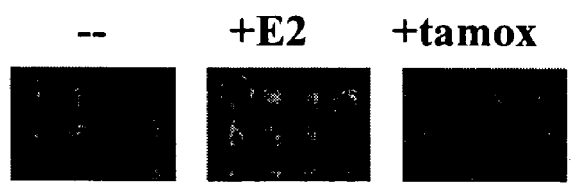
--    +E2    +tamox
C.
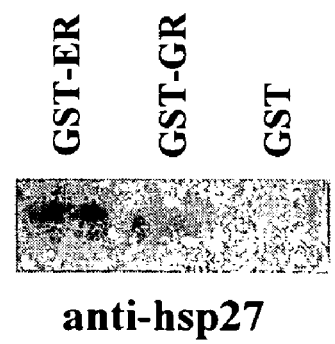
anti-hsp27
Fig. 6

*normal expression*

*'squelched' expression*

SEQUENCE LISTING

<160> NUMBER OF SEQ ID NOS: 9

<210> SEQ ID NO 1
<211> LENGTH: 202
<212> TYPE: PRT

<213> ORGANISM: Homo sapiens

<400> SEQUENCE: 1

```
Met Thr Glu Arg His Val Pro Phe Ser Leu Leu Gln Ser Pro Ser Trp
1               5                   10                  15

Asp Pro Phe Arg Asp Trp Tyr Pro His Ser His Leu Phe Asp Gln Ala
            20                  25                  30

Phe Gly Met Pro Arg Leu Pro Glu Glu Trp Ser Gln Trp Phe Gly Thr
        35                  40                  45

Ser Ser Trp Pro Gly Tyr Val Arg Pro Leu Pro Pro Thr Thr Val Glu
    50                  55                  60

Gly Pro Ala Val Ala Ala Pro Ala Tyr Ser Arg Ala Leu Asn Gln Gln
65                  70                  75                  80

Leu Ser Ser Gly Val Ser Glu Thr Ala Asp Arg Trp Arg Val Ser Leu
                85                  90                  95

Asp Val Asn His Phe Ala Pro Glu Glu Leu Thr Val Lys Thr Lys Asp
            100                 105                 110

Gly Val Val Glu Ile Thr Gly Lys His Glu Glu Arg Gln Asp Glu His
        115                 120                 125

Gly Phe Ile Ser Arg Cys Phe Thr Arg Lys Tyr Ser Leu Pro Pro Gly
    130                 135                 140

Val Asp Pro Thr Gln Val Ser Pro Ser Leu Ser Pro Glu Gly Thr Leu
145                 150                 155                 160

Thr Val Asp Ala Pro Met Ser Lys Pro Ala Thr Gln Ser Asn Glu Ile
                165                 170                 175

Thr Ile Pro Val Thr Phe Glu Ser Arg Ala Gln Leu Gly Gly Pro Glu
            180                 185                 190

Ala Ala Lys Ser Asp Arg Ser Ala Ala Lys
        195                 200
```

<210> SEQ ID NO 2
<211> LENGTH: 605
<212> TYPE: DNA
<213> ORGANISM: Homo sapiens

<400> SEQUENCE: 2

```
atgaccgagc gccacgtccc cttctcgctc ttgcagagcc ctagctggga ccccttccgc     60
gactggtacc cgcacagcca tctcttcgac caggccttcg ggatgccccg gctgccgag    120
gagtggtcgc agtggttcgg caccagcagc tggcccgggt acgtgcgccc cctgcccccc    180
accacggtcg agggccccgc ggtggccgct cccgcctaca gccgtgcgct caaccagcag    240
ctcagcagcg gggtctcgga cacggcagac cgctggcgcg tgtccctgga cgtcaaccac    300
ttcgccccg aggagctgac cgtcaagacc aaggatggcg tggtggaatc accggcaagc    360
acgaggagcg gcaggatgag cacggattca tctcccggtg tttcacccgg aaatactcgc    420
tgccccctgg tgtggacccc acccaggtct cctcctccct gtccccgag ggcacactga     480
ccgtggacgc ccccatgtcc aagccagcca cgcagtccaa cgagatcacc atccccgtca    540
ccttcgagtc gcgggcccag cttgggggcc cagaaactgc gaattccgac cggtctgcag    600
ccaag                                                                605
```

<210> SEQ ID NO 3
<211> LENGTH: 736
<212> TYPE: DNA
<213> ORGANISM: Homo sapiens -continued

```
<400> SEQUENCE: 3
agagtcagcc agcatgaccg agcgccacgt cccctttctcg ctcttgcaga gccctagctg      60
ggaccccttc cgcgactggt acccgcacag ccatctcttc gaccaggcct tcgggatgcc     120
ccggctgccc gaggagtggt cgcagtggtt cggcaccagc agctggccgg gctacgtgcg     180
ccccctgccc cccaccacgg tcgagggccc cgcggtggcc gctcccgcct acagccgtgc     240
gctcaaccag cagctcagca gcggggtctc ggagacggca gaccgctggc gcgtgtccct     300
ggacgtcaac cacttcgccc ccgaggagct gaccgtcaag accaaggatg cgtggtgga     360 atcaccggca agcacgagga gcggcaggat gagcacggat tcatctcccg gtgtttcacc     420
cggaaatact cgctgccccc tggtgtggac ccacccagg tctcctcctc cctgtccccc     480
gagggcacac tgaccgtgga cgcccccatg tccaagccag ccacgcagtc caacgagatc     540
accatccccg tcaccttcga gtcgcgggcc cagcttgggg gcccagaaac tgcgaattcc     600
gaccggtctg cagccaagta aaagccttag ccaggatacc catccgtgcc accgccactg     660
gccatacccc ccaccacctg tgtgttcttt tgatacattt atctgctttt ctcaaataaa     720
gttcaaagca accacc                                                     736

<210> SEQ ID NO 4
<211> LENGTH: 23
<212> TYPE: DNA
<213> ORGANISM: Unknown
<220> FEATURE:
<223> OTHER INFORMATION: Oligonucleotide primer

<400> SEQUENCE: 4
cgcaggagcg agaaggggac gcg                                              23

<210> SEQ ID NO 5
<211> LENGTH: 22
<212> TYPE: DNA
<213> ORGANISM: Unknown
<220> FEATURE:
<223> OTHER INFORMATION: Oligonucleotide primer

<400> SEQUENCE: 5
cgcgtcccct tctcgctcct gc                                               22

<210> SEQ ID NO 6
<211> LENGTH: 45
<212> TYPE: DNA
<213> ORGANISM: Unknown
<220> FEATURE:
<223> OTHER INFORMATION: Oligonucleotide primer

<400> SEQUENCE: 6
ggggaattcc atatgaccat gaccctccac accaaagcat caggg                      45

<210> SEQ ID NO 7
<211> LENGTH: 37
<212> TYPE: DNA
<213> ORGANISM: Unknown
<220> FEATURE:
<223> OTHER INFORMATION: Oligonucleotide primer

<400> SEQUENCE: 7 gccagggga tcctcagact gtggcaggga aaccctc                                37

<210> SEQ ID NO 8
<211> LENGTH: 28
```

```
<212> TYPE: DNA
<213> ORGANISM: Unknown
<220> FEATURE:
<223> OTHER INFORMATION: Oligonucleotide primer

<400> SEQUENCE: 8
gccgaattcg cccagcgccc cgcatttt                                          28

<210> SEQ ID NO 9
<211> LENGTH: 35
<212> TYPE: DNA
<213> ORGANISM: Unknown
<220> FEATURE:
<223> OTHER INFORMATION: Oligonucleotide primer

<400> SEQUENCE: 9
cccctcgagg gtggttgctt tgaactttat ttgag                                  35
```

INTRACELLULAR ESTRADIOL BINDING PROTEIN

This application claims the benefit of priority under 35 U.S.C. § 119 of provisional application Ser. No. 60/468,717, filed May 7, 2003, the contents of which are hereby incorporated by reference.

GOVERNMENT RIGHTS

The invention described herein arose in the course of or under Grant No. 1 RO1 DK55843-01A1 between the National Institutes of Health and the Division of Endocrinology and Metabolism at Cedars-Sinai Medical Center. The U.S. Government may thus have certain rights in this invention.

FIELD OF THE INVENTION

This invention relates to the signaling of estrogen and resistance to the same. In particular embodiments, the invention relates to an intracellular estradiol binding protein, a gene encoding the same and various cell lines overexpressing the same.

BACKGROUND OF THE INVENTION

Estrogens are clinically important in both men and women. They affect growth, differentiation, and the development of reproductive tissues, and also play a role in a variety of diseases. For instance, estrogen maintains bone density, and in the cardiovascular system, estrogen exerts anti-atherosclerotic effects by lowering circulating cholesterol levels.

Controlling the levels and/or effects of estrogen is important in most forms of breast cancer. More than 1.2 million people will be diagnosed with breast cancer this year worldwide. In the United States alone, nearly 211,300 women and 1,300 men are newly diagnosed with breast cancer each year. It is the second leading cause of cancer deaths in women today and is the most common cancer among women, excluding cancers of the skin.

Estrogen receptors are specialized proteins that bind to estrogen. These proteins are found in significant quantities within certain estrogen-sensitive tissues. Cells within breast tissue contain estrogen receptors, for example, and the binding of estrogen to the estrogen receptors stimulates these cells to proliferate. Many breast cancer tumors also contain significant levels of estrogen receptors, and are therefore called "estrogen receptor positive" ("ER+").

One conventional method used to discontinue or slow down the growth and proliferation of breast cancer cells is to reduce the effects of estrogen. The growth of ER+ breast cancer cells can generally be controlled by blocking the estrogen receptors, lowering hormone levels, and/or reducing the number of receptors available to receive growth signals. A conventional method to treat or help prevent the occurrence of breast cancer is by administering selective estrogen receptor modulators ("SERMs"), which block the estrogen receptors by preventing the growth signals from reaching the cells. SERMs target specific estrogen receptors in the body and either stimulate or depress an estrogen-like response, depending upon the particular organ. In breast cells, SERMs have antagonistic properties and block the effects of estrogen, thereby slowing the growth of breast cancer cells.

Tamoxifen (available under the trade name NOLVADEX from AstraZenica PLC; London, UK) is a commonly used SERM, which is used to treat advanced and early stage breast cancer. Tamoxifen is also used as therapy for the primary prevention of breast cancer. Although tamoxifen has been used to treat breast cancer for nearly twenty years, it has some serious drawbacks. Tamoxifen therapy may increase the risk of cancer of the uterine lining (i.e., endometrial cancer and sarcoma), blood clots within deep veins (i.e., deep vein thrombosis), blood clots in the lungs (i.e., pulmonary embolism), and cataracts. Other adverse side effects can include hot flashes, vaginal discharge, and menstrual irregularities.

Controlling the levels and/or effects of estrogen is also important in the treatment and prevention of osteoporosis. Osteoporosis is a common skeletal disorder characterized by a progressive decrease in bone mass and density; causing bones to become abnormally thin, weakened, and easily fractured. Although bone density naturally begins to decrease at approximately 35 years of age, women are disproportionately at risk for osteoporosis after menopause due to declining production of estrogen. After menopause, in women who are not receiving hormonal therapy, estradiol levels are generally about 10-20 pg/ml. The average level of estradiol needed to maintain healthy bones in menopausal women is about 40-50 pg/ml. Osteoporosis is the most significant health hazard associated with menopause; it affects 25% of women over the age of 65.

Osteoporosis is a significant public health threat for an estimated 44 million Americans. In the United States today, 10 million individuals are estimated to already have the disease, and almost 34 million more are estimated to have low bone mass, placing them at increased risk for osteoporosis. Of the 10 million Americans estimated to have osteoporosis, 8 million are women and only 2 million are men.

Because estrogen is associated with the proliferation of cells, the clinical aim in osteoporosis treatment is to increase the effect of estrogen (the opposite clinical goal of many breast cancer treatments). Conventional osteoporosis therapies include antiresorptive drugs, bone-building agents, and non-pharmacological intervention. Bisphosphonates are antiresporptive drugs that are widely used for the prevention and treatment of osteoporosis; they inhibit the breakdown and removal of bone (i.e., resorption) and are typically the first choice for osteoporosis treatment and prevention. However, in addition to adverse side effects, such as abdominal pain, nausea, and muscle and joint pain, some patients who take bisphosphonates also develop severe digestive reactions including irritation, inflammation or ulceration of the esophagus. These reactions can cause chest pain, heartburn or difficulty or pain upon swallowing. Raloxifene is another SERM commonly used to treat osteoporosis, but it carries the risk of blood clots and may cause a variety of side effects, including coughing blood, severe headaches, loss of speech, coordination or vision, pain or numbness in the arms, chest or legs, and shortness of breath. Still another conventional treatment for osteoporosis is estrogen-progestin therapy, but this approach is associated with side effects such as vaginal bleeding, bloating, nausea, headaches, and fluid retention. Estrogen-progestin therapy is no longer a first-line treatment for osteoporosis in postmenopausal women because of increases in the risk of breast cancer, stroke, blood clots, and perhaps coronary disease.

Conventional treatments for estrogen-related disease have substantial drawbacks; many are only partially effective and have adverse side effects, and few provide a cure for associated conditions. Present conventional methods to treat estrogen-related diseases may not be suitable for every patient. For the foregoing reasons and others, there is a need for a clinical intervention that can be used to control the regulation of estrogen signaling. Such an intervention would be an important tool to treat or prevent diseases and health conditions that are related to levels of estrogen; for example, breast cancer and osteoporosis. An understanding of the biomolecular pathway responsible for these conditions would be of significant importance in treating, and ultimately curing these conditions. A cell line that can be used as a clinical model in testing therapeutic interventions and diagnostic techniques would also be quite useful in this regard.

SUMMARY OF THE INVENTION

Various embodiments of the present invention provide a novel intracellular estradiol binding protein ("IEBP"), as well as the polynucleotide that encodes it. While not wishing to be bound by any theory, it is believed that the biological activity of estrogen may be modulated by IEBP as, for example, by inhibiting or enhancing its expression or signaling. More particularly, it is believed that by increasing the levels of IEBP, the signaling of estrogen is inhibited. Conversely, suppressing, inhibiting or otherwise lowering the levels of IEBP enhances estrogen signaling. IEBP binds to 17β-estradiol ($E_2$), and inhibits estrogen response element transactivation by competing with the estrogen receptor (ER) to bind to $E_2$.

Further embodiments of the present invention describe cells and cell lines that include the polynucleotide that encodes IEBP. Still further embodiments of the present invention describe cells and cell lines that produce and/or overexpress IEBP.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

FIG. 1 depicts a comparative analysis of the homology between IEBP from New World primate ("NWP") cells and human heat shock protein-27 ("hsp27") in accordance with an embodiment of the present invention. FIG. 1A depicts the full-length deduced amino acid sequence for IEBP compared to human hsp27, and the human α-crystallins A ("hCrys A") and B ("hCrys B"). The shaded areas depict regions of high sequence homology among all four molecules. The underlined regions denote areas of sequence homology with the ATP- and substrate-binding domains of human heat shock proteins in the −90 and −70 families. FIG. 1B depicts the percentage homology values for an IEBP amino acid sequence compared to hsp27, hCrys A and hCrys B.

FIG. 2 suggests that IEBP cooperates with ERE-BP to squelch ERE-directed transactivation.

FIG. 3 illustrates estrogen's role in IEBP-mediated suppression of ERE-directed transactivation and depicts an analysis of cytoplasmic binding, in accordance with an embodiment of the present invention. FIG. 3A depicts an effect of IEBP on ERE promoter-reporter luciferase activity in wild-type 6299 breast cancer cells from an Old World primate host stably transfected with vector alone (open bars) and three different subclones of cells stably transfected with the full length IEBP cDNA, in the absence (left panel) or presence (right panel) of 17β-estradiol ($E_2$ 10 nM; closed bars). Data are the mean of triplicate determinations of luciferase activity. *=statistically different from vector alone transfectants, $P<0.001$. FIG. 3B depicts displacement of [$^3$H]17β-estradiol ($E_2$) in postnuclear extracts of IEBP stably transfected cell lines. Data are the mean of triplicate determinations of % maximal [$^3$H]17β-estradiol displaced by increasing doses of $E_2$ (0.1-100 nM) in vector only controls and the three IEBP stable transfectant cell lines. FIG. 3 suggests that IEBP-mediated suppression of ERE-directed transactivation is associated with increased cytoplasmic binding of estrogen.

FIG. 4 depicts electromobility shift assays ("EMSAs") using double-strand consensus ERE as probe, and recombinant human ERα and/or ERE-affinity-purified ERE-BP as protein in accordance with an embodiment of the present invention. IEBP (lane 7, panel A; lanes 3 & 4, panel B) neither bound to ERE nor competed with the ER for binding to ERE (lane 6, panel A; lanes 2 & 3, panel C) in the presence or absence of 100 nM 17β-estradiol ($E_2$). The ER-ERE complex was supershifted by adding anti-hsp27 antibody with or without 100 nM $E_2$ (lanes 4 & 5; panel C). FIG. 4 suggests that the effects of IEBP on ERE-mediated transcription are not due to direct interaction with the ERE or disruption of ER-ERE complex formation.

FIG. 5A depicts an EMSA using double-strand consensus ERE as probe and recombinant human ERα, human hsp27 and anti-human hsp27 antibody as complexing protein in the presence or absence of 100 nM 17β-estradiol ($E_2$) in accordance with an embodiment of the present invention. FIG. 5B depicts immunoprecipitation of the protein constituents of postnuclear extracts of vector alone and IEBP-transfected Old World primate 6299 breast cancer cells with anti-human hsp27 (left panel) and anti-human ERα (right panel) followed by detection with anti-human ERα antibody and anti-human hsp27 antibody, respectively. FIG. 5 suggests that there is a direct association between the human ERα and hsp27-like proteins.

FIG. 6 depicts 17β-estradiol-regulated expression of IEBP and its interaction with ERα in accordance with an embodiment of the present invention. FIG. 6A depicts a 17β-estradiol-mediated increase in expression of hsp27 in wild-type breast cells. Shown is Western blot analysis of hsp27 in wild-type breast cells in the absence or presence of increasing doses of $E_2$ (0.1-100 nM). FIG. 6B depicts a yeast two-hybrid analysis of ligand 17β-estradiol ($E_2$)-dependent interaction of hsp27 with ERα. AH109 yeast cells were cotransfected with a Gal4 DNA binding domain-ERα fusion protein plasmid, and colonies growth-selected using Leu-/Trp-/His-/Ade-medium containing either $E_2$ (10 nM), the ER antagonist tamoxifen (Tam, 10 nM) or vehicle only (none). FIG. 6C depicts a GST pull-down analysis of ER interacting proteins. Protein extracts of cells overexpressing IEBP were incubated with either an ER-GST or glucocorticoid receptor (GR)-GST fusion protein or GST protein alone. GST-bound proteins were separated on SDS-PAGE and probed with an anti-hsp27 antibody. These results suggest that the ER-IEBP interaction is promoted by ligand 17β-estradiol but not the SERM tamoxifen.

FIG. 7 depicts normal and IEBP-mediated squelching of ER-ERE-directed transactivation in accordance with an embodiment of the present invention.

DETAILED DESCRIPTION OF THE INVENTION

Figure 2:
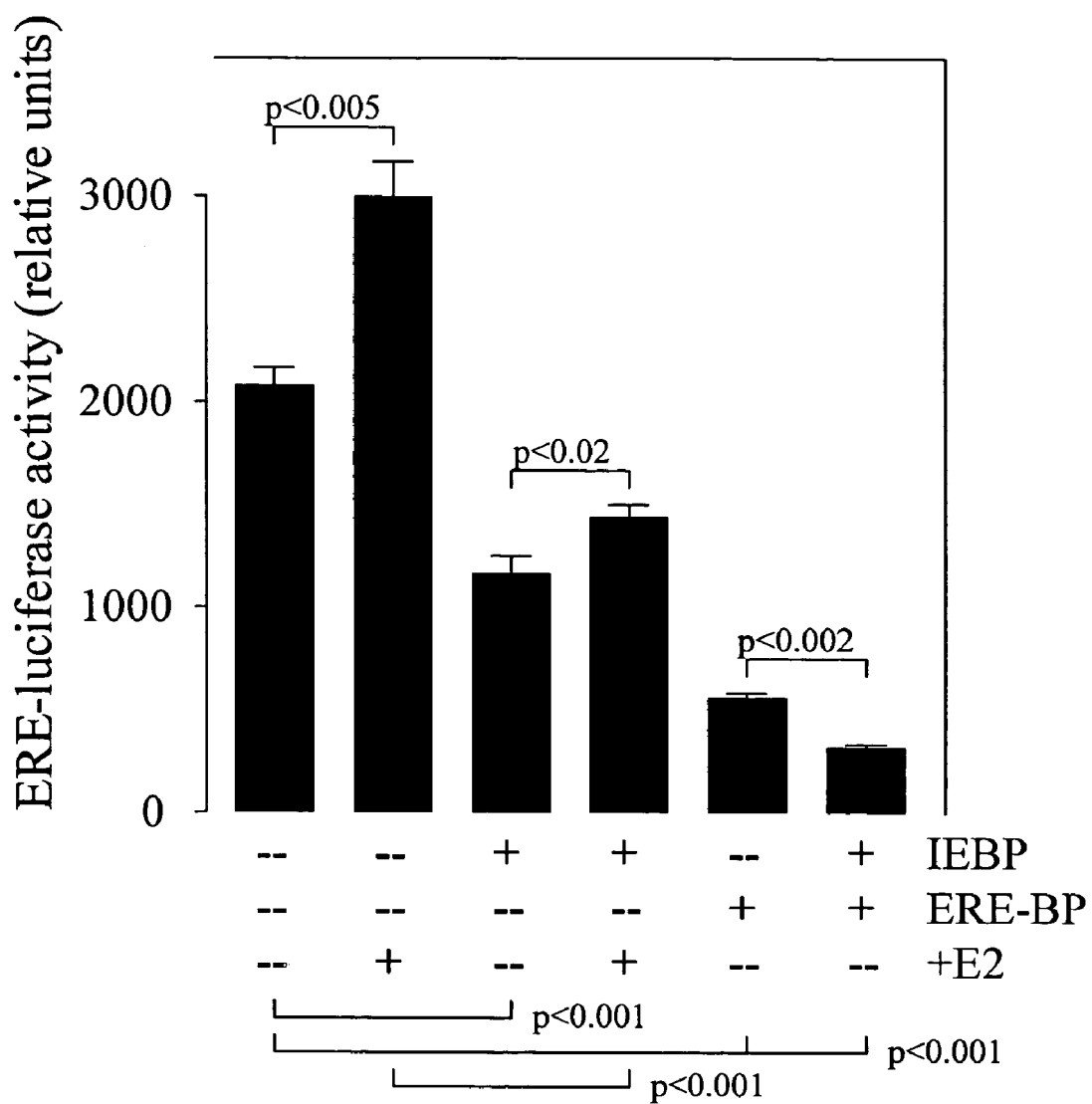
FIG. 2 depicts an analysis of estrogen response element ("ERE") luciferase activity of IEBP and estrogen response element binding protein ("ERE-BP") in accordance with an embodiment of the present invention. Expression constructs containing cDNA for the New World primate ERE-BP and/or the New World primate IEBP were transiently co-transfected with an estrogen-responsive luciferase reporter plasmid into the ERα+ human MCF-7 breast cancer cell line, in the absence or presence of 10 nM 17β-estradiol ($E_2$). Data are the mean of triplicate determinations of luciferase activity. *=statistically significant compared to control transfectants, $P<0.001$.
Figure 7A:
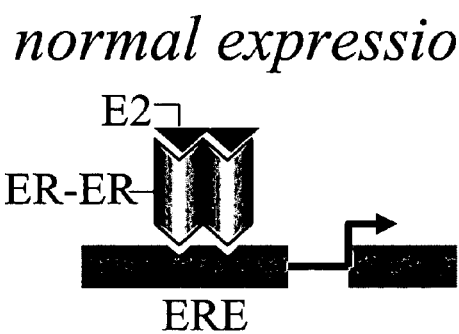
FIG. 7A depicts normal transcriptional events with 17β-estradiol ($E_2$)-bound ER homodimer interacting with ERE to increase transcription.
Figure 7B:
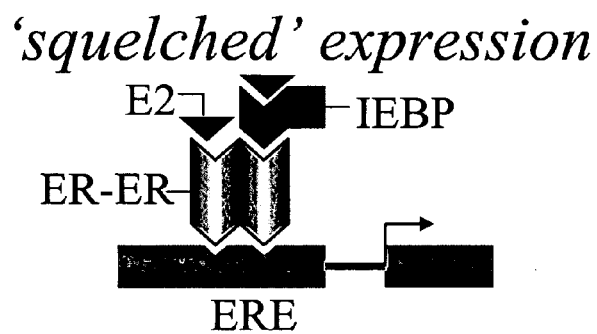
FIG. 7B depicts "squelched" transcriptional events under the influence of IEBP; the interposition of the $E_2$-binding IEBP between ER and ligand leads to disruption of ER dimerization, the ER-ERE interaction and transactivation.
Figure 8:
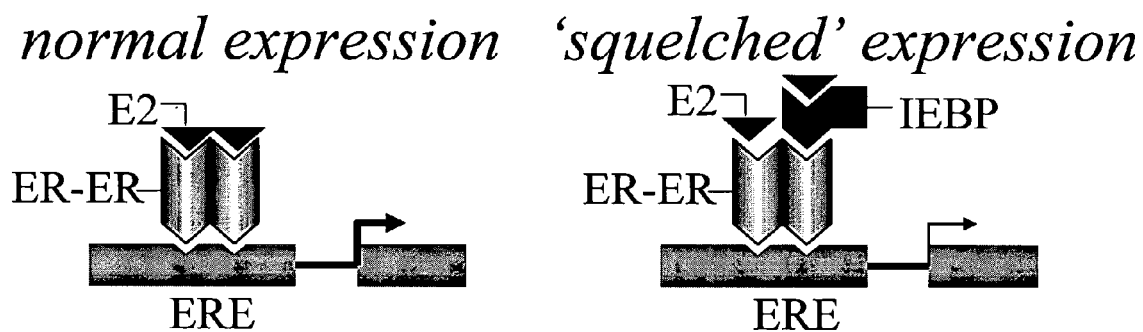

The inventors have found that methods to regulate estrogen signaling can be derived from understanding hormone resistance in New World primates. Compared to Old World primates, including man, New World primates display relative resistance to adrenal, gonadal and vitamin D sterol/steroid hormones, including 17β-estradiol. In female New World primates, this hormone-resistant phenotype is characterized by elevated concentrations of plasma estradiol and progesterone. The precise mechanism for this hormone resistance in New World primates is not fully understood, however, it does not involve aberrant expression of nuclear receptors for specific hormones, which is the principal cause of hormone resistance in humans. Instead, hormone resistance in New World primate cells appears to be due to epigenetic factors which result either in low-affinity receptor-steroid binding kinetics or attenuation of receptor-DNA interaction. For instance, studies of glucocorticoid resistance in New World primate cells have shown increased expression of the heat-shock protein (hsp)90-associated FK 506-binding immunophilin FKBP51, which inhibited ligand binding to glucocorticoid receptors by 74%.

Vitamin D resistance in New World primates appears to be due to aberrant expression of hsp-70-like intracellular vitamin D binding proteins ("IDBPs") and a dominant negative-acting vitamin D response element binding protein ("VDRE-BP"), the latter being homologous to heterogeneous nuclear ribonuclear protein A ("hnRNPA"). In a similar fashion to vitamin D, estrogen resistance in New World primates is associated with the overexpression of two compensatory proteins: an intracellular estradiol binding protein ("IEBP") and a non-receptor-related estrogen response element binding protein ("ERE-BP").

By gaining an understanding of the biochemical mechanisms behind estrogen resistance and the high levels of circulating steroid hormones in New World primates, new opportunities for treating and diagnosing diseases related to estrogen and other steroidal hormones have been achieved. The present invention is based on the surprising results of the inventors' research on estrogen resistance in New World primates. As noted above, they found that this resistance to estrogen is associated with the overexpression of two compensatory proteins: IEBP and ERE-BP.

Estrogen effects are generally mediated through the estrogen receptor ("ER"). Typically, the ER is activated when it binds to its ligand binding domain (i.e., estrogen). The classical pathway for ER signaling is mediated by receptor binding to the estrogen response element ("ERE"), which is a specific DNA sequence to which the ER binds with high affinity. The ER undergoes a conformational change as a result of ligand binding, DNA binding, and phosphorylation by cell signaling pathways. This conformational change enables it to activate transcription. If the ER ligand is inhibited or if there is not enough estrogen for the ER dimer, then ER cannot be activated and the transcription of ERE will decrease or not run.

IEBP is believed to be a member of the heat shock protein-27 ("hsp27") family. Hsp27 was first identified in extracts of human breast cancer cells as a heat shock and estrogen responsive protein; features that are characteristic of IEBP. A comparison of the homology of cDNA between human hsp27 and IEBP in New World primates suggests that there is 89.4% identity in 292 nt overlap.

As is described in further detail below, the term "IEBP" as used herein refers not only to proteins having the amino acid residue sequence of naturally occurring IEBPs (such as human hsp27 protein), but also refers to other equivalent proteins such as functional derivatives and variants of the naturally occurring or synthetic IEBP, as well as compounds with active sites that function in a manner similar to IEBP, whether these compounds are themselves naturally occurring or synthetic.

Like hsp27, IEBP expression was increased in response to heat shock. Furthermore, IEBP expression is more prominent in females than in males while diminished in the female breast after ovariectomy. These characteristics attest to the estrogen responsiveness of IEBP expression. Chen, et al., "Purification and Characterization of a Novel Intracellular 17β-Estradiol Binding Protein in Estrogen-Resistant New World Primate Cells," *J. Clin. Endocrinol. Metab.,*" 88: 501-504 (2003). While not wishing to be bound by any theory, it is believed that the hsp 27-related IEBP binds to the ligand binding domain of estrogen receptor alpha (ERα) and acts to squelch 17β-estradiol ("$E_2$")-ERα-mediated transcription. By binding to the ligand binding domain of ERα (i.e., $E_2$), it is believed that IEBP inhibits ERE transactivation because it competes with ERα for $E_2$. IEBP competes with ERα for ligand binding, squelching 17β-estradiol-ER-directed signaling. It is further believed that IEBP does not bind with ERE nor does it compete with ER to bind to ERE to inhibit transactivation.

IEBP acts as an extra-nuclear depot for estrogen binding in a manner that is distinct from the ER to which it is linked. IEBP does not appear to directly influence ERα expression. The data from the inventors' study indicate that the hsp 27-related IEBP acts as a corepressor or chaperone for the cytoplasmic ER, with either dissociation or inactivation of this function upon estrogen binding.

ERE-BP is a member of the hnRNP C (heterogeneous nuclear ribonucleoprotein) family. Although the central RNP-containing domain of ERE-BP bears a high degree of sequence similarity to other hnRNP's, it is not clear whether these same RNA binding sites are also responsible for the binding of ERE-BP to DNA. Regardless of the primary structural similarities between hnRNP's and ERE-BP, ERE differs from the classical profile of hnRNP in some aspects. For instance, ERE-BP is not confined to the nuclear compartment of the cell. Based on recent studies, ERE-BP was isolated in post-nuclear extracts of New World primate cells as well as from both the cytoplasmic and nuclear compartments of estrogen-resistant cells. Additionally, ERE-BP appears to be versatile in its ability to bind nucleic acid; ERE-BP can bind to single- or double-stranded DNA and may also interact with RNA. Chen et al., "Cloning and Expression of a Novel Dominant-Negative-Acting Estrogen Response Element-Binding Protein in the Heterogeneous Nuclear Ribonucleoprotein Family," *J Biol Chem*, 273: 31352-31357 (1998).

It is believed that ERE-BP acts to squelch ER-ERE transactivation by competing with ER to bind to ERE. ERE-BP binds to ERE, and not the ligand of $E_2$. ERE-BP acts in a dominant negative cis-acting mode to squelch transactivation by competing with ER for its response element. By acting directly with ERE and interfering with ER binding, ERE-BP silences ER action.

IEBP can cooperate with ERE-BP by acting as an intracellular repository for $E_2$ or by binding to the ligand-binding domain of ER. In either case, the net effect is that IEBP interrupts ER-ER homodimerization, thereby legislating estrogen resistance. Based on the amino acid sequence of tryptic fragments of a protein purified by $E_2$ affinity chromatography from post-nuclear extracts of estrogen-resistant NWP cells, the inventors were able to design degenerate primers that enabled amplification of an IEBP cDNA with similarity to the "small heat shock proteins," including human hsp27 and crystallins A and B (FIG. 1A). The high degree of sequence identity, 87% (FIG. 1B), between the New World primate IEBP and the human hsp27 indicates that IEBP is likely the interspecies homology of human hsp27. The family of small heat shock proteins (sHsps; 15-42 kDa), which includes hsp27, is encountered in both pro- and eukaryotes. In the human genome, hsp27 is encoded by four different genes on chromosomes 3, 7, 9 and X; such redundancy indicates that the encoded protein(s) is critical for survival of the host. Like their counterparts in the 70 kDa, 90 kDa and 60 kDa molecular weight range, the sHsps (1) are upregulated by cell "stress"; including heat stress which is transduced by heat shock factors interacting with specific heat shock enhancer elements in the promoter of hsp genes, and (2) can function as "molecular chaperones" protecting the structural and functional integrity of the intracellular proteins to which they are bound. Unlike heat shock proteins in the 70, 90 and 60 kDa families, sHsps appear to: (1) be less homologous in their amino acid sequence, (2) play a central role in preventing apoptosis, (3) be crucial for the organization of the cytoskeleton and microfilamental structures therein and (4) be needed for self-oligimerization, providing for the refractory nature of the human lens.

Although the N- and C-terminal amino acid sequences may vary considerably among sHsp family members and between species, the general domain structure of the sHsp molecules remains highly conserved through evolution. A central α-crystallin domain of ~90 residues is bounded by the variable N-terminal and C-terminal extensions. The C-terminal extension, a polar structure, is now considered to be the prime mediator of the molecules' chaperone function, while the conserved α-crystallin and variable N-terminal domains are thought to be essential for multimerization of the sHsps. In addition to being highly homologous with human hsp27, when compared to the α-crystallins (FIGS. 1A and 1B) the IEBP isolated from estrogen-resistant New World primate cells here was determined to possess the typical conserved central α-crystallin core domain flanked by variable N- and C-terminal extensions. Considering that IEBP was isolated by its ability to adhere to an $E_2$-affinity support, the IEBP sequence was scanned for the presence of an estrogen binding site. As shown in FIG. 1A, a sequence with 38% identity to a 21 amino acid stretch of the ligand binding domain of the ERα was detected in the highly conserved α-crystallin core domain of the molecule. Although formal mapping studies were not completed, it is presumed that it is this part of the IEBP, and its human homology hsp27, that is responsible for the enhancement of $E_2$ binding in cells constitutively overexpressing IEBP (FIG. 3B). Moreover, because this putative $E_2$ binding subdomain resides in the conserved α-crystallin domain of the sHsps, it is possible that estrogen binding may be a function of other members of the sHsp27 family. Although there resides some sequence identity to the ATP-binding/ATPase domain prototypical of the larger heat shock proteins (e.g., hsp70, hsp90 and hsp60) in the conserved α-crystallin domain, the role, if any, ATP has in governing the function of IEBP and other hsp70-like proteins remains to be determined.

In addition to bearing the above-mentioned enhancer cis elements that can interact with heat shock factors, the hsp 27 promoter also contains an estrogen response element (ERE) half site in direct proximity to an Sp1 site and the TATA box. While this ERE half site can be shown to interact with the ERα, $E_2$-directed transactivation of the hsp27 gene, as reported by a number of laboratories, does not require the ERE half-site. The inventors' studies confirm that the anti-human hsp27-reactive IEBP is an estrogen-responsive gene product, being markedly up-regulated after overnight exposure to ER-saturating concentrations of $E_2$ (FIG. 5A). So IEBP, and presumably its human homology hsp27, is an estrogen up-regulated gene product that can, in turn, bind the same hormone. These results indicate that $E_2$ can up-regulate expression of an $E_2$-interacting protein that, in turn, can squelch $E_2$-ERα-ERE-directed transactivation (FIGS. 2 and 3). This suggests that transcriptional down-regulation of IEBP or hsp27 gene expression might be achieved by the product of that gene through its ability to squelch, but not completely subdue (FIG. 2, bars 3 and 4) estrogen-driven expression. In other words, it is possible that hsp27 or IEBP could be auto-regulated (i.e., when $E_2$-ERα-directed hsp27 expression goes up, it produces a protein(s) that dampens subsequent $E_2$-ER enhancer action at the level of the hsp27-promoter). Such a negative feedback system would serve to reostatically regulate $E_2$-promoted transactivation.

Human breast cancers that harbor the ERα are susceptible to estrogen-directed growth advantage. This has led to the broad usage of SERMs as adjuvant chemotherapeutic agents in this disease. The mechanism(s) by which occupancy of the ERα by $E_2$ affects this change in tumor cell growth and proliferation remain an area of intense investigation. One of the genes that is activated in human ERα-expressing breast cancer cells by $E_2$ exposure is hsp27, the human homology of the New World primate IEBP reported here; similarly, estrogen-driven hsp27 expression can be squelched by exposure of cells to SERMs. This has led to the investigation of hsp27, like ERα, as a human breast cancer tumor marker with hsp27 tumor expression currently suggested to be a "downstream" indicator of estrogen-ERα interaction in tumor cells. In some, but not all studies, hsp27 expression has been shown to correlate with ERα expression. Therefore, it is of note that in the co-immunoprecipitation, yeast two-hybrid and GST pull-down assays carried out as part of the current studies (FIGS. 5B and 6) there was evidence for a direct protein-protein interaction between the hsp27-like IEBP and ERα that was promoted by the presence of $E_2$ and hindered by exposure to the clinically-useful SERM tamoxifen. These data suggest that co-expression of the ERα and IEBP by breast cancer cells may be functionally as well as temporally linked to one another. The consequences of the additive, dominant-negative-acting squelching of $E_2$-ERα-ERE-directed transcription of IEBP (hsp27) and the hnRNP-related ERE-BP on breast cancer cell behavior in vitro are currently under investigation.

The present invention thus relates to a novel IEBP and a polynucleotide that encodes the same; particularly, isolated and/or purified IEBP and its corresponding coding sequence. Further embodiments of the present invention relate to cells and cell lines that include the polynucleotide that encodes IEBP, as well as cells and cell lines that produce and/or overexpress IEBP. The inventive IEBP deduced peptide is illustrated as SEQ ID NO:1. The polynucleotide sequence that encodes this IEBP peptide is illustrated as SEQ ID NO:2. The polynucleotide sequence corresponding to a full-length cDNA for IEBP used in various embodiments of the present invention is illustrated as SEQ ID NO:3. This cDNA was cloned from the estrogen-resistant cell line B95-8, as described in greater detail in the ensuing Examples.

Use of the terms "isolated" and/or "purified" in the present specification and claims as a modifier of DNA, RNA, polypeptide or proteins means that the DNA, RNA, polypeptide or proteins so designated have been produced in such form by the hand of man, and thus are separated from their native in vivo cellular environment. As a result of this human intervention, the recombinant DNAs, RNAs, polypeptide and proteins of the invention are useful in ways described herein that the DNAs, RNAs, polypeptide or proteins as they naturally occur are not.

Presently preferred IEBP proteins of the invention include amino acid sequences that are substantially the same as the amino acid sequence SEQ ID NO:1 and fragments thereof, as well as biologically active, modified forms thereof. Those of skill in the art will recognize that numerous residues of the above-described sequences can be substituted with other chemically, sterically and/or electronically similar residues without substantially altering the biological activity of the resulting receptor species. In addition, larger polypeptide sequences containing substantially the same sequence as SEQ ID NO:1 therein (e.g., splice variants) are contemplated.

As employed herein, the term "substantially the same amino acid sequence" refers to amino acid sequences having at least about 70% identity with respect to the reference amino acid sequence, and retaining comparable functional and biological activity characteristic of the protein defined by the reference amino acid sequence. Preferably, proteins having "substantially the same amino acid sequence" will have at least about 80%, more preferably 90% amino acid identity with respect to the reference amino acid sequence; with greater than about 95% amino acid sequence identity being especially preferred. It is recognized, however, that polypeptide (or nucleic acids referred to hereinbefore) containing less than the described levels of sequence identity arising as splice variants or that are modified by conservative amino acid substitutions or by substitution of degenerate codons are also encompassed within the scope of the present invention.

The terms "biologically active" or "functional," when used herein as a modifier of the IEBP protein of this invention or polypeptide fragment thereof, refers to a polypeptide that exhibits at least one of the functional characteristics attributed to IEBP. For example, one biological activity of IEBP is the ability to impart estrogen resistance to mammalian cells when overexpressed therein.

The IEBP proteins of the invention may be isolated by methods well known in the art; for instance, by various recombinant expression systems, precipitation, gel filtration, ion-exchange, reverse-phase and affinity chromatography and the like. Other well-known methods are described, for example, in Deutscher et al., Guide to Protein Purification: Methods in Enzymology Vol. 182, (Academic Press, (1990)), which is incorporated herein by reference. Alternatively, the isolated polypeptide of the present invention can be obtained using well-known recombinant methods as described, for example, in Sambrook et al., Molecular Cloning, A Laboratory Manual, Cold Spring Harbor Laboratory Press (1989).

An example of a means for preparing the invention polypeptide(s) is to express nucleic acids encoding IEBP in a suitable host cell, such as a bacterial cell, a yeast cell, an amphibian cell (e.g., oocyte), or a mammalian cell using methods well known in the art, and recovering the expressed polypeptide, again using well known methods. The IEBP polypeptide of the invention may be isolated directly from cells that have been transformed with expression vectors as described herein. The invention polypeptide, biologically active fragments and functional equivalents thereof can also be produced by chemical synthesis. For example, synthetic polypeptide can be produced using Applied Biosystems, Inc. Model 430A or 431A automatic peptide synthesizer (Foster City, Calif.) employing the chemistry provided by the manufacturer.

Also encompassed by the term IEBP are polypeptide fragments or polypeptide analogs thereof. The term "polypeptide analog" includes any polypeptide having an amino acid residue sequence substantially identical to a sequence specifically shown herein (i.e., SEQ ID NO:1) in which one or more residues have been conservatively substituted with a functionally similar residue and which displays the ability to mimic IEBP as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue in place of a non-derivatized residue, provided that such polypeptide displays the requisite binding activity.

"Chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions of residues, relative to the sequence of a polypeptide whose sequence is shown herein, so long as the requisite activity is maintained.

The present invention also provides compositions containing an acceptable carrier and any of an isolated, purified IEBP polypeptide, an active fragment or polypeptide analog thereof, or a purified, mature protein and active fragments thereof, alone or in combination with one another. These polypeptides or proteins can be recombinantly derived, chemically synthesized or purified from native sources. As used herein, the term "acceptable carrier" encompasses any of the standard pharmaceutical carriers, such as phosphate buffered saline ("PBS") solution, water and emulsions such as an oil/water or water/oil emulsion, and various types of wetting agents.

In accordance with another embodiment of the present invention, there are provided isolated nucleic acids, which encode the IEBP proteins of the invention, and fragments thereof. The nucleic acid molecules described herein are useful for producing invention proteins when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of an IEBP gene or mRNA transcript in a given sample. The nucleic acid molecules described herein and fragments thereof are also useful as primers and/or templates in a PCR reaction for amplifying genes encoding the invention protein described herein.

The term "nucleic acid" (also referred to as polynucleotides) encompasses ribonucleic acid ("RNA") or deoxyribonucleic acid ("DNA"), probes, oligonucleotides and primers. DNA can be either complementary DNA ("cDNA") or genomic DNA (e.g., a gene encoding an IEBP protein). One means of isolating a nucleic acid encoding an IEBP polypeptide is to probe a mammalian genomic library with a natural or artificially designed DNA probe using methods well known in the art. DNA probes derived from the IEBP gene are particularly useful for this purpose. DNA and cDNA molecules that encode IEBP polypeptide can be used to obtain complementary genomic DNA, cDNA or RNA from mammalian (e.g., Old World primate, New World primate, human, mouse, rat, rabbit, pig and the like) or other animal sources, or to isolate related cDNA or genomic clones by the screening of cDNA or genomic libraries by conventional methods. Examples of nucleic acids are RNA, cDNA, or isolated genomic DNA encoding an IEBP polypeptide. Such nucleic acids may include, but are not limited to, nucleic acids comprising SEQ ID NO:2, SEQ ID NO:3, alleles thereof, or splice variant cDNA sequences thereof.

As used herein, the phrases "splice variant" or "alternatively spliced," when used to describe a particular nucleotide sequence encoding an invention polypeptide, refers to a cDNA sequence that results from the well known eukaryotic RNA splicing process. The RNA splicing process involves the removal of introns and the joining of exons from eukaryotic primary RNA transcripts to create mature RNA molecules of the cytoplasm. Methods of isolating splice variant nucleotide sequences are well known in the art. For example, one of skill in the art may employ nucleotide probes derived from the IEBP encoding DNA of SEQ ID NO:2, SEQ. ID NO:3, alleles thereof, splice variants thereof or fragments thereof about 10 to 150 nucleotides long and their antisense nucleic acids to screen the cDNA or genomic library of the same or other species as described herein.

In one embodiment of the present invention, DNAs encoding the IEBP protein of this invention comprise SEQ. ID NO:2, SEQ. ID NO:3, alleles thereof, splice variants thereof and fragments thereof and antisense nucleic acids thereof.

As employed herein, the term "substantially the same nucleotide sequence" refers to DNA having sufficient identity to the reference polynucleotide such that it will hybridize to the reference nucleotide under moderately stringent hybridization conditions. In one embodiment, DNA having substantially the same nucleotide sequence as the reference nucleotide sequence encodes substantially the same amino acid sequence as that set forth in SEQ ID NO:1, or a larger amino acid sequence including SEQ ID NO:1. In another embodiment, DNA having "substantially the same nucleotide sequence" as the reference nucleotide sequence has at least 60% identity with respect to the reference nucleotide sequence. DNA having at least 70%, more preferably at least 90%, yet more preferably at least 95% identity to the reference nucleotide sequence is preferred.

The present invention also encompasses nucleic acids which differ from the nucleic acids shown in SEQ ID NO:2 and SEQ ID NO:3, but which have the same phenotype. Phenotypically similar nucleic acids are also referred to as "functionally equivalent nucleic acids." As used herein, the phrase "functionally equivalent nucleic acids" encompasses nucleic acids characterized by slight and non-consequential sequence variations that will function in substantially the same manner to produce the same protein product(s) as the nucleic acids disclosed herein. In particular, functionally equivalent nucleic acids encode polypeptides that are the same as those disclosed herein or that have conservative amino acid variations, or that encode larger polypeptides that include SEQ ID NO:1. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding IEBP polypeptides that, by virtue of the degeneracy of the genetic code, do not necessarily hybridize to the invention nucleic acids under specified hybridization conditions. Preferred nucleic acids encoding the IEBP polypeptide of the invention comprise nucleotides encoding SEQ ID NO:1 and fragments thereof. Exemplary nucleic acids encoding an IEBP protein of the invention may be selected from the following:

(a) DNA encoding the amino acid sequence set forth in SEQ ID NO:1,
(b) DNA that hybridizes to the DNA of (a) under moderately stringent conditions, wherein said DNA encodes biologically active IEBP, and
(c) DNA degenerate with respect to either (a) or (b) above, wherein said DNA encodes biologically active IEBP.

As used herein, the term "degenerate" refers to codons that differ in at least one nucleotide from a reference nucleic acid (e.g., SEQ ID NO:2 or SEQ ID NO:3), but encode the same amino acids as the reference nucleic acid. For example, codons specified by the triplets "UCU," "UCC," "UCA" and "UCG" are degenerate with respect to each other since all four of these codons encode the amino acid serine.

Hybridization refers to the binding of complementary strands of nucleic acid (i.e., sense:antisense strands or probe: target-DNA) to each other through hydrogen bonds; similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As is known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of lower stringency, followed by washes of varying, but higher stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formamide, 5× Denhart's solution, 5×SSPE, 0.2% SDS at 42° C., followed by washing in 0.2×SSPE, 0.2% SDS at 65° C.

The phrase "high stringency hybridization" refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C.

The phrase "low stringency hybridization" refers to conditions equivalent to hybridization in 10% formamide, 5× Denhart's solution, 6×SSPE, 0.2% SDS at 42° C., followed by washing in 1×SSPE, 0.2% SDS at 50° C. Denhart's solution and SSPE are well known to those of skill in the art as are other suitable hybridization buffers. See, e.g., Sambrook et al., supra.

Preferred nucleic acids encoding the invention polypeptide(s) hybridize under moderately stringent, preferably high stringency conditions to substantially the entire sequence or substantial portions (i.e., typically at least 15-30 nucleotides of SEQ ID NO:2 or SEQ ID NO:3, although longer fragments are also contemplated as being within the scope of the present invention in this regard).

Site-directed mutagenesis of any region of IEBP cDNA is contemplated herein for the production of mutant IEBP cDNAs. For example, the Transformer Mutagenesis Kit (available from Clontech) can be used to construct a variety of mis-sense and/or nonsense mutations to IEBP cDNA.

The inventive nucleic acids can be produced by a variety of methods well known in the art (e.g., the methods described herein, employing PCR amplification using oligonucleotide primers from various regions of SEQ ID NO:2, and the like).

In accordance with a further embodiment of the present invention, optionally labeled IEBP-encoding cDNAs or fragments thereof can be employed to probe a library(ies) (e.g., cDNA, genomic and the like) for additional nucleic acid sequences encoding related novel mammalian IEBP proteins. Construction of mammalian cDNA and genomic libraries, preferably a human library, is well-known in the art. Screening of such a cDNA or genomic library is initially carried out under low-stringency conditions, which comprise a temperature of less than about 42° C., a formamide concentration of less than about 50% and a moderate to low salt concentration.

Presently preferred probe-based screening conditions comprise a temperature of about 37° C., a formamide concentration of about 20% and a salt concentration of about 5× standard saline citrate (SSC; 20×SSC contains 3M sodium chloride, 0.3M sodium citrate; pH 7.0). Such conditions will allow the identification of sequences which have a substantial degree of similarity with the probe sequence, without requiring perfect homology. The phrase "substantial similarity" refers to sequences which share at least 50% homology. Preferably, hybridization conditions will be selected that allow the identification of sequences having at least 70% homology with the probe, while discriminating against sequences which have a lower degree of homology with the probe. As a result, nucleic acids having substantially the same (i.e., similar) sequences as the coding region of the nucleic acids of the invention are obtained.

As used herein, a nucleic acid "probe" is single-stranded DNA or RNA or analogs thereof that has a sequence of nucleotides that includes at least 14, preferably at least 20, more preferably at least 50, contiguous bases that are the same as (or the complement of) any 14 or more contiguous bases set forth in any of SEQ ID NO:2 or SEQ ID NO:3. Preferred regions from which to construct probes include 5' and/or 3' coding regions of SEQ ID NO:2. In addition, the entire cDNA encoding region of an invention IEBP protein, or the entire sequence corresponding to SEQ ID NO:2 or SEQ ID NO:3, may be used as a probe. Probes may be labeled by methods well-known in the art, as described hereinafter, and used in various diagnostic kits.

In accordance with yet another embodiment of the present invention, there is provided a method for the recombinant production of the IEBP protein of the invention by expressing the above-described nucleic acid sequences in suitable host cells. Any cell or cell line may be used as a host cell in accordance with alternate embodiments of the present invention to create a cell or cell line that produces or overexpresses IEBP. The modified cells or cell lines generated from the host cells may be, for example, estrogen-responsive (e.g., Old World primate 6299 breast cells) or estrogen-resistant (e.g., B95-8 cells). Such cells and cell lines may be used, for example, in the screening of pharmaceutical preparations or to generate significant quantities of IEBP for inclusion in various inventive compositions. Other uses for these cells and cell lines will be readily apparent to those of skill in the art. Recombinant DNA expression systems that are suitable to produce IEBP proteins described herein are also well known in the art. For example, the above-described nucleotide sequences can be incorporated into vectors for further manipulation. As used herein, "vector" (or "plasmid") refers to discrete elements that are used to introduce heterologous DNA into cells for either expression or replication thereof.

Suitable expression vectors are well-known in the art, and include vectors capable of expressing DNA operatively linked to a regulatory sequence, such as a promoter region that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors are well known to those of skill in the art and include those that are replicable in eukaryotic cells and/or prokaryotic cells and those that remain episomal or those which integrate into the host cell genome. In addition, vectors may contain appropriate packaging signals that enable the vector to be packaged by a number of viral virions (e.g., retroviruses, herpes viruses, adenoviruses) resulting in the formation of a "viral vector."

As used herein, a "promoter region" refers to a segment of DNA that controls transcription of DNA to which it is operatively linked. The promoter region includes specific sequences that are sufficient for RNA polymerase recognition, binding and transcription initiation. In addition, the promoter region includes sequences that modulate this recognition, binding and transcription initiation activity of RNA polymerase. These sequences may be cis-acting or may be responsive to trans-acting factors. Promoters, depending upon the nature of the regulation, may be constitutive or regulated. Exemplary promoters contemplated for use in the practice of the present invention include the SV40 early promoter, the cytomegalovirus ("CMV") promoter, the mouse mammary tumor virus ("MMTV") steroid-inducible promoter, Moloney murine leukemia virus ("MMLV") promoter and the like.

As used herein, the term "operatively linked" refers to the functional relationship of DNA with regulatory and effector nucleotide sequences, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA.

As used herein, "expression" refers to the process by which polynucleic acids are transcribed into mRNA and translated into peptides, polypeptide or proteins. If the polynucleic acid is derived from genomic DNA, expression may, if an appropriate eukaryotic host cell or organism is selected, include splicing of the mRNA.

Prokaryotic transformation vectors are well-known in the art and include pBlueskript and phage Lambda ZAP vectors (available from Stratagene; La Jolla, Calif.) and the like. Other suitable vectors and promoters are described in detail in U.S. Pat. No. 4,798,885, the disclosure of which is incorporated herein by reference in its entirety.

Other suitable vectors for transformation of *E. coli* cells include the pET expression vectors (available from Novagen; see U.S. Pat. No. 4,952,496); for example, pET11a, which contains the T7 promoter, T7 terminator, the inducible *E. coli* lac operator and the lac repressor gene, and pET 12a-c, which contain the T7 promoter, T7 terminator and the *E. coli* ompT secretion signal. Another suitable vector is the pIN-IIIompA2 (see Duffaud et al., Meth. in Enzymology, 153:492-507, 1987), which contains the Ipp promoter, the lacUV5 promoter operator, the ompA secretion signal and the lac repressor gene.

Exemplary eukaryotic transformation vectors include the cloned bovine papilloma virus genome, the cloned genomes of the murine retroviruses and eukaryotic cassettes such as the pSV-2 gpt system (described by Mulligan and Berg, 1979, Nature, vol. 277:108-114), the Okayama-Berg cloning system (Mol. Cell Biol. Vol. 2:161-170, 1982) and the expression cloning vector described by Genetics Institute (Science, vol. 228:810-815, 1985). Each is available and provides substantial assurance of at least some expression of the protein of interest in the transformed eukaryotic cell line.

Particularly preferred base vectors that contain regulatory elements that can be linked to the invention IEBP-encoding DNAs for transfection of mammalian cells are CMV promoter-based vectors, such as pcDNA1 (available from Invitrogen; San Diego, Calif.); MMTV promoter-based vectors, such as pMAMNeo (available from Clontech) and pMSG (available from Pharmacia; Piscataway, N.J.); and SV40 promoter-based vectors, such as pSVβ (available from Clontech).

In accordance with another embodiment of the present invention, there are provided "recombinant cells" containing the nucleic acid molecules (i.e., DNA or mRNA) of the present invention. Methods of transforming suitable host cells, preferably bacterial cells, and more preferably *E. coli* cells, as well as methods applicable for culturing said cells containing a gene encoding a heterologous protein, are generally known in the art. See, e.g., Sambrook et al., supra.

Exemplary methods of introducing (transducing) expression vectors containing invention nucleic acids into host cells to produce transduced recombinant cells (i.e., cells containing recombinant heterologous nucleic acid) are well-known in the art (see, e.g., Friedmann, 1989, Science, 244:1275-1281; Mulligan, 1993, Science, 260:926-932, each of which is incorporated herein by reference in its entirety). Exemplary methods of transduction include, for instance, infection employing viral vectors (see, e.g., U.S. Pat. Nos. 4,405,712 and 4,650,764), calcium phosphate transfection (see, e.g., U.S. Pat. Nos. 4,399,216 and 4,634,665), dextran sulfate transfection, electroporation, lipofection (see, e.g., U.S. Pat. Nos. 4,394,448 and 4,619,794), cytofection, particle bead bombardment and the like. The heterologous nucleic acid can optionally include sequences that allow for its extrachromosomal (i.e., episomal) maintenance, or the heterologous DNA can be caused to integrate into the genome of the host (as an alternative means to ensure stable maintenance in the host).

Host organisms contemplated for use in the practice of the present invention include those organisms in which recombinant production of heterologous proteins has been carried out. Examples of such host organisms include bacteria (e.g., *E. coli*), yeast (e.g., *Saccharomyces cerevisiae, Candida tropicalis, Hansenula polymorpha* and *P. pastoris*; see, e.g., U.S. Pat. Nos. 4,882,279, 4,837,148, 4,929,555 and 4,855,231), mammalian cells (e.g., B95-8, Old World primate 6299, HEK293, CHO and Ltk cells), insect cells and the like. Presently preferred host organisms are bacteria. The most preferred bacteria is *E. coli*.

In one embodiment, nucleic acids encoding the IEBP proteins of the invention may be delivered into mammalian cells, either in vivo or in vitro using suitable viral vectors well-known in the art, e.g., retroviral vectors, adenovirus vectors and the like.

Viral based systems provide the advantage of being able to introduce relatively high levels of the heterologous nucleic acid into a variety of cells. Suitable viral vectors for introducing IEBP nucleic acid encoding an IEBP protein into mammalian cells are well known in the art. These viral vectors include, for example, Herpes simplex virus vectors (e.g., Geller et al., 1988, Science, 241:1667-1669), Vaccinia virus vectors (e.g., Piccini et al., 1987, Meth. in Enzymology, 153:545-563); CMV vectors (Mocarski et al., Viral Vectors; Y. Gluzman and S. H. Hughes, Eds., Cold Spring Harbor Laboratory, Cold Spring Harbor, N.Y., 1988, pp. 78-84), MMLV vectors (Danos et al., 1980, Proc. Nat'l. Acad. Sci. USA, 85:6469), adenovirus vectors (e.g., Logan et al., 1984, Proc. Nat'l. Acad. Sci. USA, 81:3655-3659; Jones et al., 1979, Cell, 17:683-689; Berkner, 1988, Biotechniques, 6:616-626; Cotten et al., 1992, Proc. Nat'l. Acad. Sci. USA, 89:6094-6098; Graham et al., 1991, Meth. Mol. Biol., 7:109-127), adeno-associated virus vectors, retrovirus vectors and the like. See, e.g., U.S. Pat. Nos. 4,405,712 and 4,650,764. Especially preferred viral vectors are the adenovirus and retroviral vectors.

As used herein, "retroviral vector" refers to the well-known gene transfer plasmids that have an expression cassette encoding an heterologous gene residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764). Suitable retroviral vectors for use herein are described, for example, in U.S. Pat. No. 5,252,479, and in WIPO publications WO 92/07573, WO 90/06997, WO 89/05345, WO 92/05266 and WO 92/14829, incorporated herein by reference, which provide a description of methods for efficiently introducing nucleic acids into human cells using such retroviral vectors. Other retroviral vectors include, for example, the MMTV vectors (e.g., Shackleford et al., 1988, Proc. Nat'l. Acad. Sci. USA, 85:9655-9659) and the like.

EXAMPLES

The following examples illustrate the biological activity of IEBP, as well as methods for preparing cells and cell lines that produce and/or overexpress IEBP. In the following examples, where indicated, experimental means were compared statistically using an unpaired Student's t-test.

Example 1

Cell Culture

All cell lines were obtained from American Type Culture Collection (ATCC; Rockville, Md.). The estrogen-resistant NWP cell line B95-8, derived from the hormone resistant common marmoset (*Callithrix jacchus*), was maintained in RPMI-1640 medium. The estrogen-responsive OWP breast cell line 6299, derived from a rhesus monkey (*Macaca mulatta*), was maintained in DMEM (Irvine Scientific Irvine; Calif.). All cultures were routinely supplemented with 10% fetal calf serum (FCSl, Gemini Bioproducts; Calabasas, Calif.), 100 units/ml penicillin, 100 µg/ml streptomycin, 2 mM L-glutamine (both from GIBCO-BRL; Grand Island, N.Y.) and in atmosphere of 95% air, 5% $CO_2$. In some experiments, confluent cultures were preincubated for up to 48 hours in medium containing $E_2$ (10 nM) prior to harvest and preparation of extracts.

Example 2

Preparation of Cellular Extracts

Postnuclear extracts of each cell line were prepared as described in Chen et al., "Vitamin D and Gonadal Steroid-Resistant New World Primate Cells Express an Intracellular Protein Which Competes with the Estrogen Receptor for Binding to Estrogen Response Element," *J Clin Invest*, 99: 669-675 (1997). Harvested cells were washed twice in ice-cold phosphate-buffered saline (PBS) and twice washed with ETD buffer (1 mM EDTA, 10 mM Tris-HCL, 5 mM dithiothreitol (pH 7.4)) containing 1 mM phenylmethylsulfonylflouride (PMSF). The cell pellets were then resuspended in ETD buffer and homogenized on ice in five 10-second bursts. Nuclei, with associated nuclear steroid receptor proteins, were pelleted at 10,000×g for 30 min at 4° C.

Example 3

Molecular Cloning of the IEBP by Rapid Amplification of Complementary Ends (RACE)

In previous studies, the inventors identified and characterized tryptic fragments of an $E_2$-affinity column purified protein which corresponded to the putative IEBP in NWP B95-8 cells. Chen, et al., "Purification and Characterization of a Novel Intracellular 17β-Estradiol Binding Protein in Estrogen-Resistant New World Primate Cells," *J. Clin. Endocrinol. Metab.*, 88: 501-504 (2003). To clone the mRNA corresponding to this protein they used degenerate oligonucleotides corresponding to the amino acid sequence of tryptic peptides to carry out RACE generation of candidate cDNA. Sequence analysis of the resulting deduced amino acid sequence for IEBP (FIG. 1A) revealed 87% sequence identity to the human hsp27, 40% sequence identity to human α-crystallin chain A and 44% sequence identity to chain B (FIG. 1B). The amino-acid sequence also exhibited 28-38% identity with a 21 amino-acid overlap in the ligand-binding domain of ERα, but there was no LXXLL motif typical of the steroid hormone receptor (data not shown).

Based on the amino acid of the N-terminal tryptic peptide (RVPFSL) of IEBP, the inventors designed an IEBP-specific sense oligonucleotide primer and its reversion antisense primer for 5' and 3'-RACE. Poly (A)+ RNA (2.5 µg) from B95-8 cells was used as the template to generate the 5'- and 3'-ends of the IEBP cDNA with a BD MARATHON cDNA amplification kit (Clontech Laboratories Inc.; Palo Alto, Calif.). Second-strand cDNA synthesis and adapter ligation were performed as instructed in the enclosed manual. The adapter-ligated cDNA was then used as a template for annealing adapter- and IEBP-specific primers for the RACE reaction: 5'-CGCAGGAGCGAGAAGGGGACGCG-3' (SEQ ID NO:4) and 5'-CGCGTCCCCTTCTCGCTCCTGC-3' (SEQ ID NO:5) for the 5'- and 3'-RACE of IEBP, respectively. A cDNA for the IEBP was generated by end-to-end amplification using specific 5' and 3' primers. The amplified products were then subcloned into the pcDNA 3.1/V5/His/TOPO expression vector and sequenced by the Cedars-Sinai Medical Center Sequencing Core Facility using dye terminator cycle sequence reactions and ABI automated sequencers.

Example 4

Transient Transfections $5 \times 10^5$ estrogen-resistant NWP B95-8 or estrogen-responsive OWP breast 6299 cells were seeded into 6-well plates in phenol red-free medium containing 10% charcoal-stripped fetal calf serum ("FCS") and allowed to proliferate to 80-90% confluence. Transfections were performed in triplicate with the combinations of DNA preparations set forth in Table 1 to a maximum final concentration of 20 µg DNA/ml in LIPOTAXI solution (Stratagene; La Jolla, Calif.).

TABLE 1

DNA Preparations Used to Perform Transfections i. 5.5 µg ERE-luciferase reporter plasmid
ii. 0.5 µg ERα expression plasmid (pRShER)
iii. 5.0 µg of IEBP or ERE-BP plasmid (in cDNA3.1his/v5 TOPO vector)

TABLE 1-continued

DNA Preparations Used to Perform Transfections iv. 5.0 µg β-galactosidase expression construct as internal control
v. pGEM-3z vector DNA as carrier (Promega, Madison, MI).

An equal volume of 20% FCS-supplemented, antibiotic-free medium was added to each well 5 hours after transfection followed by the addition of 10 nM $E_2$. After an additional 48 hours at 37° C., the cells were lysed, and luciferase and β-galactosidase activities were measured (FIG. 2).

Example 5

Generation of Cell Lines Overexpressing IEBP $E_2$-responsive OWP breast cells from cell line 6299 were incubated with 5.0 ug pcDNA3.1/v5-His-TOPO IEBP plasmid in LIPOTAXI solution for 5 hours followed by the addition of equal volume of 20% FCS-supplemented medium. After incubation overnight, cells were split (1:10 ratio) and incubated with fresh medium containing 500 ug/ml of the geneticin-selective antibiotic G418 sulfate (Life Technology; Grand Island, N.Y.). This medium was replaced every 3-4 days, until stable colonies formed. Single colonies were picked, transferred into a new dish, and incubated with medium containing selection antibiotic G418 until confluence for further study.

Example 6

Ligand Binding Analysis

Specific $[^3H]17\beta$-estradiol ("$[^3H]E_2$") binding was measured in postnuclear extracts of vector-alone and the three IEBP stably transfected cell lines (FIG. 3B). Briefly, postnuclear extracts isolated as described above were reconstituted in NaCl-containing ETD buffer (pH 8.0) to achieve a final salt concentration of 0.5M NaCl, and incubated overnight at 4° C. with 4 nM $[^3H]E_2$ in the presence or absence of 0.1-100 nM unlabeled competitive ligand. Protein-bound $[^3H]E_2$ was separated from unbound sterol by incubation with dextran-coated charcoal. Experiments were conducted in triplicate.

Example 7

Western Blot Analysis

Denatured cell extracts or purified protein were subjected to electrophoresis using 4-12% SDS-polyacrylamide gels and transferred to nitrocellulose membranes as described in Chen et al., "Cloning and Expression of a Novel Dominant-Negative-Acting Estrogen Response Element-Binding Protein in the Heterogeneous Nuclear Ribonucleoprotein Family," *J Biol Chem*, 273: 31352-31357 (1998). The membranes were blocked with 5% nonfat dry milk for 1 hour and then incubated with monoclonal anti-human hsp27 antibody (Santa Cruz Biotechnology Inc; Santa Cruz, Calif.; hereinafter "Santa Cruz") for 2 hours and with HRP-conjugated secondary antibody for another 1 hour prior to detection of antibody-reactive proteins with chemiluminescence reagent (ECL; Amersham Pharmacia Biotech).

Example 8

Immunoprecipitation

Cells were washed with PBS twice and lysed with RIPA buffer (1×PBS containing 1% nonidet p-40, 0.5% sodium deoxycholate, 0.1 mM PMSF, 30 µl/ml of aprotinin, and 10 mM sodium orthovanadate) (obtained from Sigma-Aldrich Corp.; St. Louis, Mo.) by incubation on ice for 10 minutes. The resulting lysates were then disrupted by repeated aspiration through a 23 gauge needle and cell supernatants obtained by centrifugation (14,000×g for 10 minutes). Aliquots of supernatant (containing 50 µg protein each) were then incubated with anti-ERα or anti-hsp27 antibody overnight at 4° C. 20 µl of protein A/G agarose (obtained from Santa Cruz) was added and incubated at 4° C. for another hour. The protein mixtures were then washed by repeated centrifugation in RIPA buffer (×4) and PBS (×1). The resulting pellet was resuspended in 2×SDS sample buffer. After boiling, sampled were analyzed by 4-20% SDS-PAGE and separated proteins transferred to nitrocellulose membranes. Western blot analyses were then carried out using anti-ERα and anti-hsp27 antibodies and visualized by ECL (FIG. 5).

Example 9

Yeast Two-Hybrid Screening

The full-length ERα cDNA was amplified using the oligonucleotides 5'-GGGGAATTCCATATGACCATGAC-CCTCCACACCAAAGCATCAGGG-3' (SEQ ID NO:6) and 5'-GCCAGGGGGATCCTCAGACTGTGGCAGG-GAAACCCTC-3' (SEQ ID NO:7). The ERα cDNA was cloned into the Nde I and Bam HI site of GAL4 DNA binding domain vector (GAL4 DNA-BD/ER). The full length human hsp27 cDNA was amplified using oligonucleotides 5'-GCCGAATTCGCCCAGCGCCCCGCATTTT-3' (SEQ ID NO:8) and 5'-CCCCTCGAGGGTGGT-TGCTTTGAACTTTATTTGAG-3' (SEQ ID NO:9). The IEBP cDNA was cloned into EcORI and XhoI site of GAL4 DNA activation domain vector. GAL4 DNA-BD/ER was cotransformed with the GAL4 DNA-AD/hsp27 plasmid using Yeast Transformation System 2 kit (obtained from Clontech; Palo Alto, Calif.) according to manufacturer's instructions; some of the plates were treated with water (control), $E_2$ (10-100 nM) or tamoxifen (10-100 nM).

The plasmids were confirmed by automated sequencing. Yeast two-hybrid analysis using the Yeast Two-Hybrid System 3 kit (obtained from Clontech) was performed according to manufacturer's instructions; again, with the exception that the plates were treated with water, $E_2$ (10-100 nM) or tamoxifen (10-100 nM).

Example 10

GST-Pull-Down Assay

A GST-fusion protein with the ligand-binding domain ("LBD") of ERα (residues 246-595) was expressed in *E coli* strain DH5α and purified by glutathione sepharose beads according to manufacturer's instructions (Pharmacia Biotech; Piscataway, N.J.). Postnuclear extracts were applied to the GST beads and incubated for 1 hour. The loaded GST-extract mixture was then washed repetitively (5×) with PBS buffer containing 5 mM DTT and 1 mM PMSF and resuspended in 2×SDS sample buffer and boiled for 5 minutes.

Denatured proteins were resolved on 4-20% SDS-PAGE gel, transferred to a nitrocellulose membrane, probed with appropriate antibody (obtained from Santa Cruz) and visualized by ECL.

Example 11

Expression of IEBP

Previously reported purification of IEBP using $E_2$-affinity column extractions confirmed its high capacity for estrogen binding but did not clarify the functional relevance of the protein in NWP cells. Experiments were therefore carried out to clarify whether the overexpression of IEBP antagonized, facilitated, or did nothing to estrogen-induced transactivation. Estrogen-responsive Old World primate cells were transiently co-transfected with IEBP cDNA and an ERE-promoter-reporter construct. After transfection, ERE-directed luciferase activity was reduced 50% compared to vector alone-transfected Old World primate cells. Overexpression of ERE-BP also suppressed ERE-mediated transcription, and when IEBP and ERE-BP were co-transfected there was an additive decrease in ERE luciferase reporter activity. The effect of IEBP was partially abrogated but not restored to normal by pre-treatment with $E_2$, which also stimulated ERE-mediated transcription in control cells. Similar results were also obtained following stable transfection of IEBP into Old World primate cells. Increased expression of IEBP in these cells was confirmed by Western blot analyses using an anti-hsp27 antibody. These studies also showed that $E_2$ stimulated hsp27 expression in a dose-dependent fashion in wild-type control cells. Subsequent promoter-reporter data showed that ERE luciferase reporter activity decreased 2-3 fold in the presence of IEBP when compared with wild-type cells. As with the transient transfectants, this effect was only partially abrogated by pre-treatment with $E_2$. Using the stable transfectant variants, it was also possible to assess the relationship between IEBP-modulated transcription and postnuclear binding of $E_2$.

Example 12

Characterization of IEBP

Analysis of both transient and stable transfectants indicated that IEBP acts to squelch ERE-directed gene transcription. This is believed to be due, at least in part, to enhanced binding of estrogens. To determine whether IEBP also functions as a direct competitor for ERE-binding, the inventors carried out electrophoretic mobility shift analyses (EMSAs) using an idealized ERE as a probe with recombinant ERα and/or postnuclear extracts from OWP-IEBP stable transfectant clone 1 as binding proteins. Data showed that IEBP neither bound to ERE nor competed with the ERα for binding to ERE. Although IEBP did not appear to bind directly to the ERE, its ability to squelch ER-mediated transcription was consistent with possible direct interaction with the ERα. To assess this possibility, coimmunoprecipitation was performed by using anti-ERα and anti-hsp27 antibodies. Antihuman ERα antibodies were used to immunoprecipitate ERα-untreating proteins in postnuculear extracts of both wild-type and IEBP-stably-transfected cells. The immunoprecipitates were subjected to Western blot analysis by using hsp27 antibodies. Data confirmed association between ERα and hsp27. Similar results were also obtained following initial immunoprecipitation with hsp27, and subsequent ERα blotting.

Example 13

Ligand-Dependent Interaction of ERα with hsp27

In contrast to the IEBP transfectants, there was relatively little association between ERα and hsp27 in extracts from untreated wild-type cells. However, data indicated the overnight treatment of wild-type cells (but not IEBP transfectants) with $E_2$ strongly increased hsp27 expression, highlighting the possible importance of ligand in determining ER-Hsp27/IEBP interaction. The yeast two-hybrid system was therefore employed to confirm ligand-dependent interaction with the ERα. Full-length ERα cDNA was cloned as a fusion protein with the GAL4 activation domain, and was used in yeast co-transformations. To identify proteins that interact with ERα in a ligand specific fashion, yeast colonies were selected on SD leu-/trp-/His-/Ade-medium supplemented with or without 10 nM $E_2$ or tamoxifen. The full-length hsp27 and ER insert grew only in the presence of $E_2$. No growth was observed in the presence of the ER antagonist tamoxifen or in selective media without $E_2$.

Lastly, in order to confirm the interaction between hsp27 and ER, GST-pull-down assays were performed. Protein extracts of cells overexpressing IEBP were incubated with a GST-receptor ligand-binding domain fusion protein representing the ER. Control assays were employed using a glucocorticoid receptor (GR)-fusion protein or GST protein alone. In each case, SDS-PAGE separation that showed the hsp27 was assessed using anti-hsp27 antibody. Data showed that hsp27 was only pulled-down by the ER-GST but not GR-GST, or GST alone.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

What is claimed is:

1. An isolated polypeptide, comprising an intracellular estradiol binding protein (IEBP) as set forth in SEQ ID NO:1.

2. An isolated polypeptide, comprising an intracellular estradiol binding protein (IEBP) that has at least 90% identity to the amino acid sequence set forth in SEQ ID NO:1 wherein the IEBP is capable of binding to estradiol.

3. The isolated polypeptide of claim 2, wherein the IEBP has at least 95% identity to the amino acid sequence set forth in SEQ ID NO: 1.

4. A composition comprising:

an isolated polypeptide, comprising an intracellular estradiol binding protein (IEBP) that has at least 90% identity to the amino acid sequence set forth in SEQ ID NO:1 wherein the IEBP is capable of binding to estradiol; and a carrier.

5. The composition of claim 4, wherein said isolated polypeptide is an IEBP polypeptide that has at least 95% identity to the amino acid sequence set forth in SEQ ID NO:1.

6. The composition of claim 4, wherein said isolated polypeptide consists of the sequence set forth in SEQ ID NO:1.

7. The composition of claim 4, wherein said carrier is selected from the group consisting of phosphate buffered saline (PBS) solution, water, emulsions, and wetting agents, and combinations thereof.

* * * * *